(12) United States Patent
Wong et al.

(10) Patent No.: US 9,408,642 B2
(45) Date of Patent: Aug. 9, 2016

(54) VERTEBRAL OSTEOSYNTHESIS ASSEMBLY FORMED BY A VERTEBRAL OSTEOSYNTHESIS MATERIAL AND INSTRUMENTS FOR PLACING SAID MATERIAL

(75) Inventors: Chung Chek Wong, Kuching (MY); Jean-Louis Labbe, Noumea (FR); Julius Fernandez, Memphis, TN (US); Victor Hsu, Ambler, PA (US)

(73) Assignee: MEDICREA INTERNATIONAL, Neyron (FR)

( * ) Notice: Subject to any disclaimer, the term of this patent is extended or adjusted under 35 U.S.C. 154(b) by 124 days.

(21) Appl. No.: 13/817,895

(22) PCT Filed: Aug. 30, 2011

(86) PCT No.: PCT/IB2011/053796
§ 371 (c)(1),
(2), (4) Date: Feb. 20, 2013

(87) PCT Pub. No.: WO2012/029025
PCT Pub. Date: Mar. 8, 2012

(65) Prior Publication Data
US 2013/0150898 A1   Jun. 13, 2013

(30) Foreign Application Priority Data
Sep. 1, 2010   (FR) ..................................... 10 56930

(51) Int. Cl.
*A61B 17/70* (2006.01)
(52) U.S. Cl.
CPC ......... *A61B 17/7076* (2013.01); *A61B 17/7041* (2013.01); *A61B 17/7083* (2013.01); *A61B 17/7086* (2013.01); *A61B 17/7004* (2013.01); *A61B 17/7011* (2013.01)

(58) Field of Classification Search
USPC ........................................................ 606/86 A
See application file for complete search history.

(56) References Cited

U.S. PATENT DOCUMENTS

| 5,782,831 A | * | 7/1998 | Sherman et al. ............ 606/86 A |
| 2004/0138662 A1 | * | 7/2004 | Landry et al. .................. 606/61 |

(Continued)

FOREIGN PATENT DOCUMENTS

| EP | 1 415 603 A2 | 5/2004 |
| WO | WO 98/55038 A1 | 12/1998 |
| WO | WO 2009/011929 A1 | 1/2009 |

OTHER PUBLICATIONS

Dec. 1, 2011 International Search Report issued in International Patent Application No. PCT/IB2011/053796.

(Continued)

*Primary Examiner* — Jan Christopher Merene
(74) *Attorney, Agent, or Firm* — Oliff PLC

(57) ABSTRACT

In this assembly; each connecting piece comprises engaging means situated outside said conduit for engaging a connecting bar and outside said conduit for engaging on an anchor member, making it possible to grasp said connecting piece using a handling instrument. The assembly comprises at least one handling instrument comprising engaging means complementary to those comprised by each connecting piece. According to the invention, each anchor member is equipped with a proximal shaft, the length of which is such that it protrudes past the patient's skin after implantation of said anchor member on a vertebra. Each handling instrument is tubular and can be engaged on the proximal shaft of each anchor member so as to allow the movement of a connecting piece grasped by the instrument along the proximal shaft of each anchor member.

8 Claims, 12 Drawing Sheets

(56) References Cited

U.S. PATENT DOCUMENTS

| | | | |
|---|---|---|---|
| 2004/0249378 A1* | 12/2004 | Saint Martin et al. | 606/61 |
| 2006/0036252 A1 | 2/2006 | Baynham et al. | |
| 2006/0084979 A1* | 4/2006 | Jackson | 606/61 |
| 2006/0106380 A1 | 5/2006 | Colleran et al. | |
| 2006/0293693 A1* | 12/2006 | Farr et al. | 606/104 |
| 2007/0233155 A1 | 10/2007 | Lovell | |
| 2009/0062859 A1* | 3/2009 | Mahoney et al. | 606/278 |
| 2009/0062860 A1* | 3/2009 | Frasier et al. | 606/278 |
| 2009/0082812 A1* | 3/2009 | Lewis | 606/281 |
| 2010/0331897 A1* | 12/2010 | Lindner | 606/305 |
| 2011/0093014 A1* | 4/2011 | Davis et al. | 606/259 |
| 2011/0112580 A1* | 5/2011 | Clement et al. | 606/264 |
| 2012/0209332 A1* | 8/2012 | Janowski | 606/278 |
| 2012/0303062 A1* | 11/2012 | Amstutz et al. | 606/267 |
| 2013/0184759 A1* | 7/2013 | Rinehart et al. | 606/266 |

OTHER PUBLICATIONS

Dec. 1, 2011 Written Opinion of the International Searching Authority issued in International Patent Application No. PCT/IB2011/053796.

\* cited by examiner

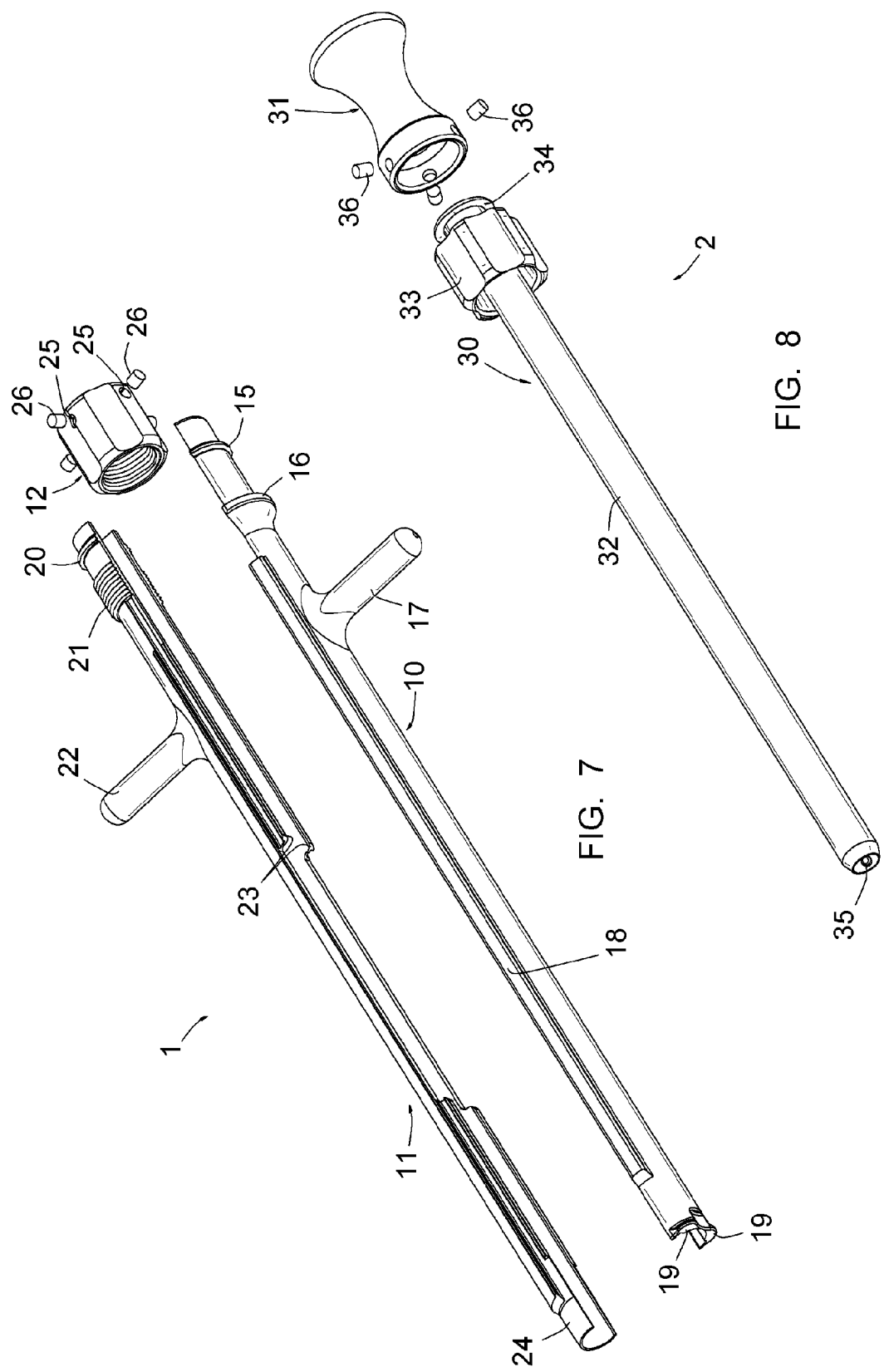

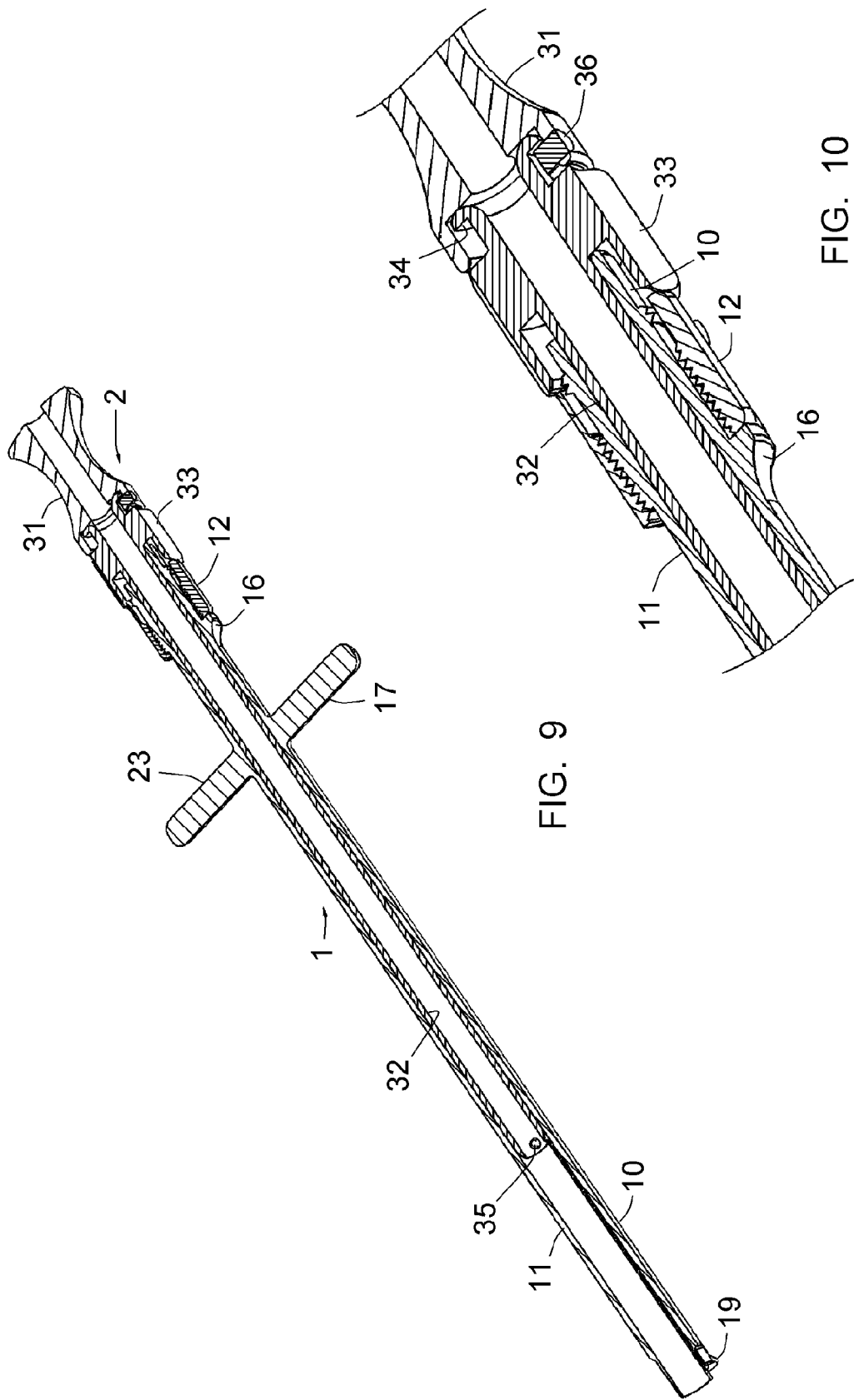

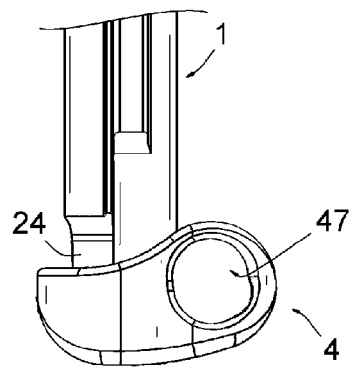
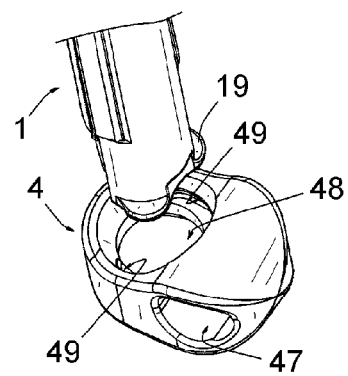
FIG. 11        FIG. 12
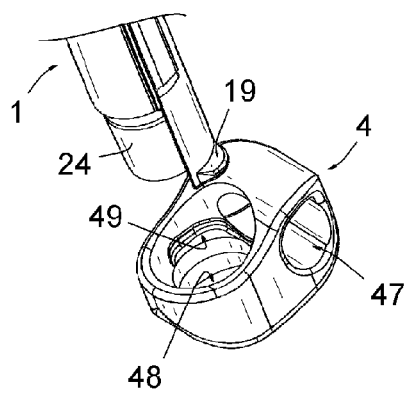
FIG. 13
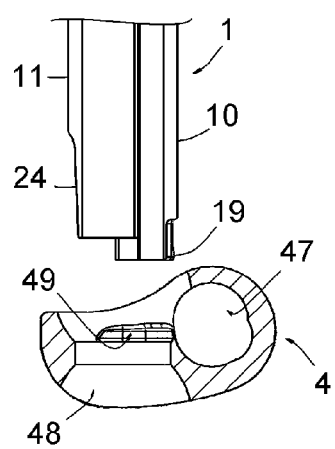 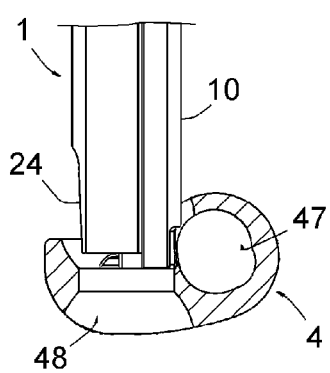 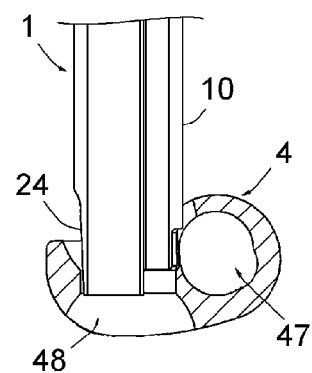
FIG. 14        FIG. 15        FIG. 16

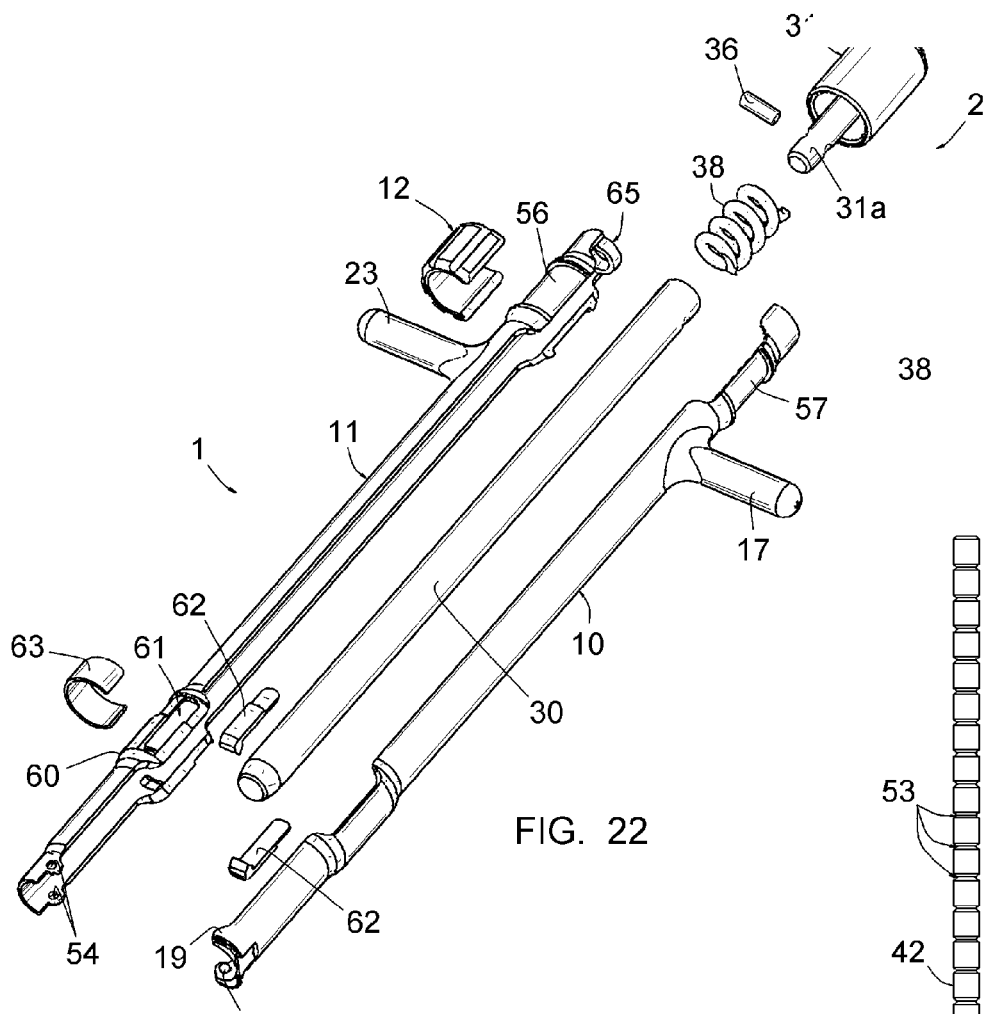
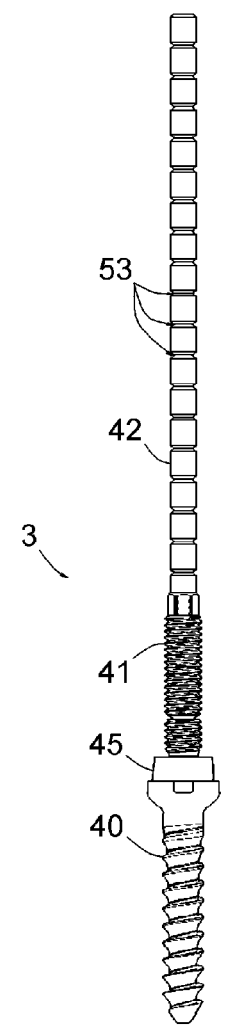
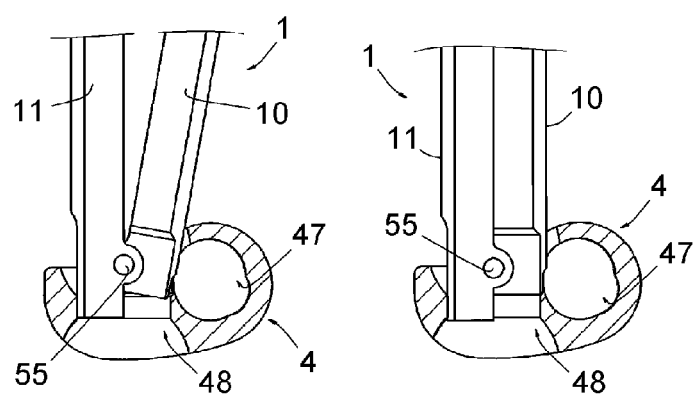
FIG. 22
FIG. 23　　FIG. 24　　FIG. 21

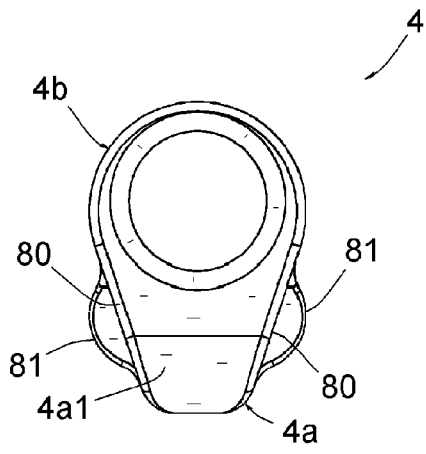
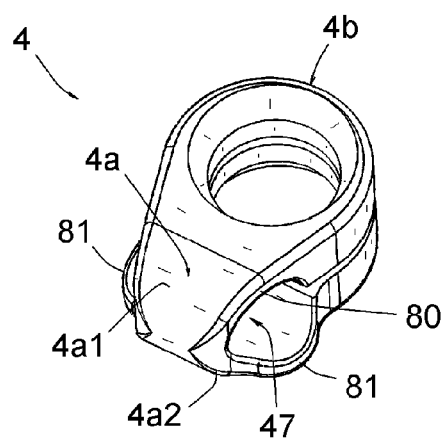
FIG. 32          FIG. 33
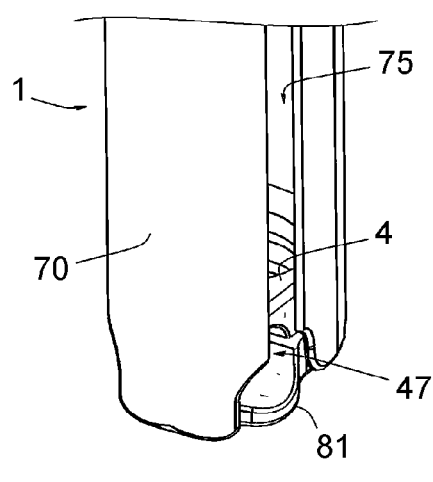
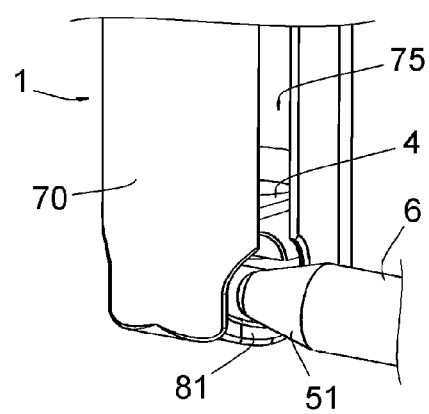
FIG. 34          FIG. 35

VERTEBRAL OSTEOSYNTHESIS ASSEMBLY FORMED BY A VERTEBRAL OSTEOSYNTHESIS MATERIAL AND INSTRUMENTS FOR PLACING SAID MATERIAL

The present invention relates to a vertebral osteosynthesis assembly formed by a vertebral osteosynthesis material and instruments for placing said material. It also relates to a percutaneous vertebral osteosynthesis surgical method.

It is well known to immobilize two or more vertebrae using a vertebral osteosynthesis material comprising (i) anchoring members for anchoring to the vertebrae, in particular in the form of polyaxial pedicular screws, (ii) at least one connecting bar intended to connect several consecutive anchor members, (iii) connecting pieces making it possible to connect said connecting bar to said anchor members, and (iv) immobilizing nuts for immobilizing the connecting pieces on the anchor members. Document no. WO 98/55038, for example, describes such material.

One traditional technical for placing such a material consists of making a large incision opposite the vertebrae to be treated, performing dissections of the tissues surrounding these vertebrae so as to expose them, placing the anchor members on the vertebrae through a direct approach, engaging the connecting pieces on the connecting bar, then lowering said assembly toward the anchor members, so as to engage the connecting pieces on the proximal pins comprised by the anchor members, putting the nuts in place, and lastly closing said incision.

This technique has the drawbacks of generating notable traumas on the tissues surrounding the vertebrae, sources of post-operatory pain, and leaving a large scar on the patient's back.

To resolve these drawbacks, so-called "percutaneous" techniques have been designed, the principle of which is to make only small incisions opposite each implantation zone of an anchor member, placing anchor members in the form of so-called "tulip" or "top loading" screws, i.e. defining proximal transverse channels for engaging a connecting bar, crossing the axis of the screw, engaging the connecting bar percutaneously in the different transverse channels of said screws, then immobilizing said connecting bar in the channels by placing threaded stoppers on the proximal parts of the screws.

According to a first of these "percutaneous" techniques, the connecting bar is obliquely inserted into the channel of a screw situated at one end of the assembly, then is pushed toward the successive channels of the other screws, the forward end of the bar dissecting the tissues from one screw to the next. This technique has the significant drawbacks of causing noticeable difficulties to blindly engage the connecting bar with the channels of the successive screws, and thereby causing non-negligible trauma to the tissues surrounding the insertion area of the bar as well as the tissues surrounding the vertebrae. Furthermore, instruments for placing screws have large diameters and are also the cause of significant dissections of the tissues and exert noticeable traumas thereon.

According to a second of these "percutaneous" techniques, for example described by document US 2006/0106380, the connecting bar is inserted more or less vertically at a screw situated at one end of the assembly, then is pivoted so as to allow its forward end to be engaged in the channel of said first screw and is then slid toward the successive channels of the other screws. This technique has substantially the same drawbacks as the first cited technique.

According to a third of these "percutaneous" techniques, described by document WO 2009/011929, a screw is put into place with a connecting piece placed on it, then a connecting bar secured to another connecting piece and is introduced more or less vertically at one end of the assembly, then is pivoted so as to allow the forward end of said bar to engage through the connecting piece mounted on the screw, and a screw is then placed through said other connecting piece. This technique has substantially the same drawbacks as the other cited techniques. This document also describes means for grasping of a connecting piece by an instrument, as mentioned in the preamble of the appended claim 1.

The present invention aims to resolve the aforementioned drawbacks, by providing a material and instruments making it possible to install the material using a "percutaneous" technique, with an easy connection of a connecting bar with the corresponding anchor members, and generating lesions or traumas that are as reduced as possible to the tissues surrounding the vertebrae.

The concerned assembly comprises, in a known manner, a material comprising anchoring members for anchoring to the vertebrae, in particular in the form of polyaxial pedicular screws, at least one connecting bar intended to connect several consecutive anchor members, and connecting pieces making it possible to connect said connecting bar to said anchor members, each connecting piece comprising a conduit for engaging a connecting bar and a conduit for engaging on an anchor member;

each connecting piece comprises engaging means situated outside said conduit for engaging a connecting bar and outside said conduit for engaging on an anchor member, making it possible to grasp said connecting piece using a handling instrument, this grasping immobilizing the connecting piece relative to the handling instrument and not presenting an obstacle, once done, to the engagement of the connecting bar in said engaging conduit or the engagement of the connecting piece on the corresponding anchor member;

the assembly comprises at least one handling instrument as previously mentioned, comprising engaging means complementary to those comprised by each connecting piece, to perform said grasping, and locking means making it possible to selectively engage said handling instrument with a connecting piece and disengage it from said connecting piece, so as to make it possible to selectively grasp the connecting piece with the instrument and separate it therefrom.

According to the invention, each anchor member is equipped with a proximal shaft, the length of which is such that it protrudes past the patient's skin after implantation of said anchor member on a vertebra; and each handling instrument is tubular and can be engaged on the proximal shaft of each anchor member so as to allow the movement of a connecting piece grasped by the instrument along the proximal shaft of each anchor member.

The assembly according to the invention makes it possible to implement an original percutaneous vertebral osteosynthesis method, consisting of:

making only small incisions opposite each implantation area of an anchor member on a vertebra;

placing the anchor members on the vertebrae to be treated;

using said at least one handling instrument, engaging at least one connecting piece, grasped by said instrument, on a proximal shaft then through an incision and positioning said piece just under the patient's skin;

introducing the connecting bar just under the patient's skin, then in said engaging conduit comprised by each connecting piece;

repeating, if necessary, the two operations described above as many times as necessary to engage the required number of connecting pieces on the connecting bar;

moving the assembly formed by the connecting bar and several connecting pieces toward the receiving surfaces for the connecting pieces comprised by said anchor members;

immobilizing the connecting pieces relative to the anchor members using immobilization members comprised by the material;

closing said incisions.

The invention thus consists of using not "tulip" screws, but screws receiving connecting pieces to connect them to a connecting bar, and using at least one tubular handling instrument making it possible to grasp at least one connecting piece so as to engage a connecting bar with one or more of these connecting pieces immediately under the patient's skin, then moving the assembly thus formed along proximal shafts comprised by the anchor members, toward receiving surfaces for receiving the connecting pieces, comprised by said anchor members. The engagement of the connecting bar with the connecting pieces is done easily due to the fact that the connecting pieces are located immediately under the patient's skin: the connecting bar therefore has a small incline relative to the connecting pieces during said insertion, which greatly facilitates this insertion, unlike the existing techniques, in which, given that the "tulip" screws are placed on the vertebrae, there is a significant level difference between the channels comprised by these screws and the cutaneous insertion area for the connecting bar. Furthermore, with the assembly according to the invention, the instruments make it possible to position the connecting pieces perfectly relative to the connecting bar. This ease of insertion of the connecting bar greatly reduces, compared to the aforementioned existing techniques, the lesions or traumas caused to the tissues surrounding the vertebrae, both between the anchor members and at the insertion area of the connecting bar, and also reduces the duration of the operation.

With the technique according to the invention, the dissection of the tissues is done either before introduction of the connecting pieces and the connecting bar, or by moving the connecting bar and connecting pieces toward the anchor members, therefore in the longitudinal direction of the muscular fibers. Such a dissection leads to reduced traumas on the tissues surrounding the vertebrae.

Moreover, the use of connecting pieces of the "side loading" type, i.e. in each of which the conduit for engaging the connecting bar is laterally offset relative to the conduit for engaging on the anchor member, advantageously makes it possible to arrange said engaging means comprised by a connecting piece on the margin of the conduit for engaging on the anchor member, and therefore to have a handling instrument whereof the transverse section does not exceed the periphery of the connecting piece. This instrument can therefore have a reduced section, not traumatizing for the tissues, in particular a cylindrical shape with a diameter smaller than or equal to 8 mm.

According to one possible embodiment of said engaging means, each connecting piece comprises two cavities formed in its wall extending between said conduit for engaging the connecting bar and said conduit for engaging on the anchor member, laterally relative to said conduit for engaging on the anchor member, and the handling instrument comprises two protrusions intended to be placed in said cavities in an adjusted manner.

According to one possible embodiment of the handling instrument in this case, the instrument comprises a first elongate piece including said protrusions, and said locking means comprised by said instrument are formed by a second elongate piece, axially mobile relative to the first elongate piece; said second elongate piece can be moved relative to the first elongate piece between a withdrawn position, in which it makes it possible to engage with and disengage from said protrusions and said cavities, and a forward position, in which it occupies said engaging conduit and keeps said protrusions and cavities mutually engaged.

According to another possible embodiment of the handling instrument in that same case, the handling instrument comprises a first elongate piece having said protrusions, and said locking means comprised by said instrument are formed by a second elongate piece, pivotably connected to said first elongate piece; these elongate pieces can pivot relative to each other between a mutually separated position, in which said protrusions and said cavities can engage and disengage, and a mutually close position, in which said protrusions and cavities are kept mutually engaged.

Preferably, each handling instrument can slidingly engage with the proximal head of an anchor member, either directly or via an engaging instrument comprised by the material, able to engage slidingly with the proximal shaft, on the one hand, and to engage with the handling instrument on the other hand.

Perfect guiding of the connecting pieces toward said receiving surfaces is thus achieved.

Preferably,
- each proximal shaft comprises, on the length thereof, means for controlled advancement of the handling instrument, and if applicable of each engaging instrument, along the length thereof, and
- the assembly according to the invention comprises controlled advancement means complementary to those of said shaft.

These controlled advancement means allow a controlled descent, in particular step by step, of each connecting piece along a proximal shaft, thereby enabling a progressive and controlled dissection of the tissues.

According to one embodiment of the invention in that case, the controlled advancement means comprise:
- a helical track formed in one said proximal shaft, and
- lugs secured to said engaging instrument, able to slide in the track.

Preferably,
- each proximal shaft comprises, on the length thereof, means for immobilizing the handling instrument, and if applicable said engaging instrument, in a given position along the length thereof, and
- the handling instrument, or if applicable said engaging instrument, comprises immobilizing means complementary to those of said shaft.

These immobilizing means enable immobilization of a connecting piece in a given position, thereby enabling a gradual placement of the connecting bar and connecting pieces, and thereby making it possible to correct the position of the vertebrae.

According to one preferred embodiment of the invention in this case, said controlled advancement means and said immobilizing means comprised by a proximal shaft comprise stepped grooves arranged in said proximal shaft and hooks formed on said engaging instrument, able to engage with or disengage from said grooves.

According to another embodiment of the invention, each handling instrument comprises at least one distal slot for guiding a slender forward end comprised by the end of the connecting bar intended to be engaged through a connecting piece grasped by said handling instrument, said slot emerging in the distal end of the instrument and having a widened end portion, the opening of the connecting piece intended to receive the connecting bar being located in coincidence with said widened portion when said connecting piece is grasped by the handling instrument.

Perfect guiding of the connecting bar toward said opening is thus achieved.

This slot also has the advantage of imparting slight radial flexibility to the tubular body of the instrument, making it possible to grasp the connecting piece by simple wedging of said connecting piece in the distal end of the instrument. The latter can thus have a purely tubular structure, which is therefore extremely simple.

The handling instrument can comprise a single slot or two slots situated on two opposite sides thereof.

Preferably, the connecting piece intended to be used with this slotted handling instrument comprises a first portion defining said conduit for engaging a connecting bar and a second portion defining said conduit for engaging on an anchor member; said first portion comprises an upper part whereof the width is smaller than that of said second portion, and a lower part whereof the width is larger than that of said second portion; the width of said upper part is such that, when the connecting piece is grasped using the instrument, this upper part does not form an obstacle to be overcome by said slender forward end comprised by the connecting bar; the width of said lower part is such that, also when the connecting piece is grasped using the instrument, said lower part forms a stop for receiving said slender forward end.

Thus, said slender forward end comprised by the end of the connecting bar can be slid in the slot without encountering obstacles, therefore without any risk of loss of the guiding allowed by the slot, until said slender forward end abuts against said lower part; in this position, this slender forward end is perfectly positioned opposite said engaging conduit, through which it is intended to be inserted.

It will be understood that the terms "upper" and "lower" respectively refer to the side of the connecting piece that is spaced away from the vertebra after placing the material on said vertebra, and the side of the connecting piece that faces said vertebra after said placement. The term "width" refers to the dimension of said first portion in a direction parallel to said engaging conduit of a connecting bar.

According to one embodiment of this connecting piece, said upper part of the first portion is laterally defined by two straight edges converging toward each other moving away from said second portion, and said lower part of the first portion has at least one boss laterally protruding from said lower part, i.e. in a direction parallel to the axis of said engaging conduit of a connecting bar.

The invention will be understood, and other features and advantages thereof will appear, in reference to the appended diagrammatic drawing, showing, as non-limiting examples, two embodiments of the concerned vertebral osteosynthesis assembly.

FIGS. 1 and 2 are side views of a handling instrument and engaging instrument, respectively, comprised by the material, according to a first embodiment;

FIGS. 3 to 6 are side views of different pieces forming a vertebral osteosynthesis material, according to a first embodiment, i.e.: FIG. 3: a screw to be implanted in a vertebra; FIGS. 4 and 5: two types of connecting pieces making it possible to connect a connecting bar to a plurality of screws according to FIG. 3; FIG. 6: a connecting bar to connect several screws according to FIG. 3 using connecting pieces according to FIG. 4 or FIG. 5;

FIGS. 7 and 8 are exploded perspective views, respectively, of said handling instrument and said engaging instrument;

FIG. 9 is a longitudinal cross-sectional view, in the assembled state, of said handling instrument and said engaging instrument, the engaging instrument being engaged in the handling instrument;

FIG. 10 is a partial view, similar to FIG. 9, of these same instruments, on an enlarged scale;

FIGS. 11 to 13 are side and perspective views, respectively, of the distal end of the handling instrument and a connecting piece;

FIGS. 14 to 16 are side views of the distal end of the handling instrument and a connecting piece, during three successive steps of the grasping of said connecting piece by the handling instrument;

FIG. 21 is a side view, similar to FIG. 3, of a screw according to a second embodiment;

FIG. 22 is an exploded perspective view of the handling instrument and the engaging instrument according to a second embodiment;

FIGS. 23 and 24 are views respectively similar to FIGS. 15 and 16, showing two successive steps in the grasping of the connecting piece by the handling instrument according to the second embodiment;

FIG. 32 is a top view of another connecting piece that can be used with the instrument according to FIG. 26;

FIG. 33 is a perspective view of this other connecting piece;

FIG. 34 is a perspective view of the distal end of the instrument according to FIG. 26, with said other connecting piece inserted therein; and FIG. 35 is similar to FIG. 34, while a connecting bar is ready to be engaged in an engaging conduit comprised by said other connecting piece to receive the connecting bar.

Figure 1:
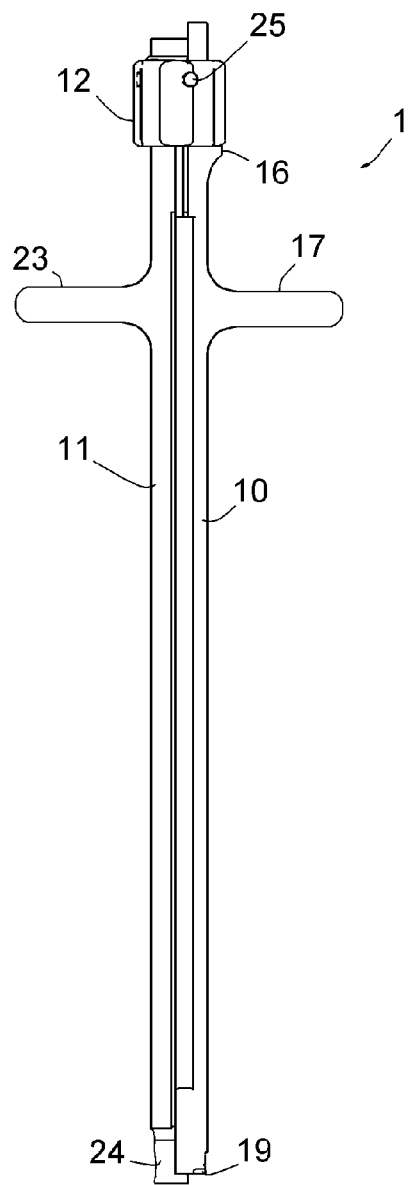
Figure 2:
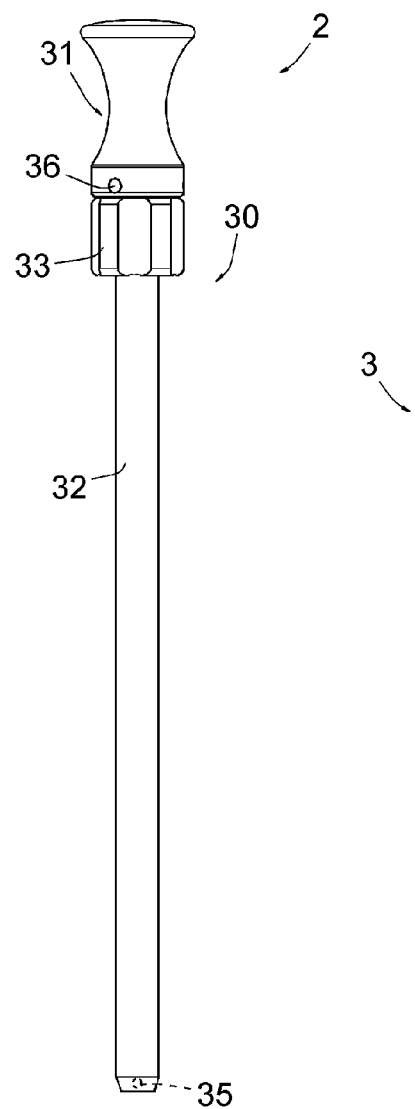
Figure 3:
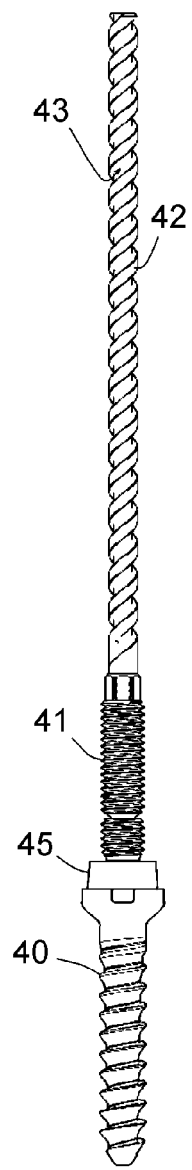
Figure 4:
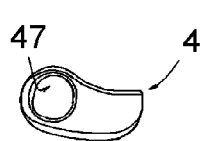

Out of simplification, the parts or elements of one embodiment that are found identically or similarly in another embodiment will be designated using the same numerical references and will not be described again.

FIGS. 1 to 6 show different component elements of a vertebral osteosynthesis assembly. This vertebral osteosynthesis assembly comprises a plurality of handling instruments 1 such as that shown in FIG. 1, a plurality of engaging instruments 2 such as that shown in FIG. 2, a plurality of screws 3 like those shown in FIG. 3, a plurality of connecting pieces 4, 5 like those shown in FIG. 4 or FIG. 5, and one or two connecting bars 6 like those shown in FIG. 6.

In reference to FIGS. 1 and 7, it appears that each handling instrument 1 essentially comprises a first elongate piece 10, a second elongate piece 11 and a ring 12.

The first elongate piece 10 has, over all of its length, a general semi-tubular shape, i.e. has a curved wall defining a longitudinal inner cavity. It comprises a widened proximal part comprising two stop flange rings 15, 16, a grasping arm 17, perpendicular thereto, two longitudinal parts 18 jointly forming a guideway, and two distal protrusions 19. The latter, more particularly visible in FIGS. 12 and 13, extend in planes perpendicular to the longitudinal axis of the piece 10, laterally relative thereto, and are rounded, thereby forming a "pair of ears."

The second elongate piece 11 has, over all of its length, a general semi-tubular shape similar to that of the piece 10, able to form a tube with the latter when it is assembled therewith. It comprises a widened proximal part comprising a stop flange ring 20 identical to the flange ring 15, a threaded portion 21 distant from said flange ring 20, a grasping arm 22, perpendicular thereto, two longitudinal parts 23 forming skates able to slide in the guideway formed by the parts 18 of the piece 10 and a smooth distal part 24.

As shown in FIGS. 7 and 10, the ring 12 is outwardly knurled and inwardly comprises a smooth proximal part and a threaded distal part. At its proximal part, it comprises four radial holes 25 in which slugs 26 can be driven.

It is understood in reference to FIGS. 7, 9 and 10 that the pieces 10 and 11 are assembled by engagement of the longitudinal parts 23 forming skates in the guideway formed by the parts 18, then by engagement of the ring 12 on the proximal parts of said pieces 10, 11. The ring 12 is engaged on the piece 10 until it abuts against the flange ring 16 and said ring 12 is screwed on the threaded portion 21 of the piece 11. In this stop position of the ring 12 against the flange ring 16 and screwing on the threaded portion 21, the holes 25 are located beyond, in the distal direction, the flange rings 15 and 20; thus slugs 26 are then driven through said holes 25, which produces an axial immobilization of the ring 12 on the piece 10 and makes it impossible for the piece 11 to escape even in case of complete unscrewing of the ring 12 relative to the threaded portion 21, the slugs 26 abutting against the flange ring 20 in that case.

It is understood that the rotation of the ring 12 makes it possible to slide the piece 11 longitudinally relative to the piece 10, between a withdrawn position visible in FIG. 14 and an extended position visible in FIG. 16.

In reference to FIGS. 2 and 8 to 10, it appears that the engaging instrument 2 essentially comprises a tubular elongate piece 30 and a handle 31. The piece 30 comprises a tubular part 32, a proximal knurl 33 secured to said tubular part 32, a proximal flange ring 34 separated from the knurl 33 by a groove and two distal lugs 35 able to slide in a helical track 43 comprised by a proximal shaft 42 secured to the screw 3. The handle 31 comprises a distal housing for receiving the flange ring 34 and radial holes intended to receive slugs 36 driven therein. These slugs 36 allow a pivoting assembly of the handle 31 on the proximal end of the piece 30.

As shown in FIGS. 9 and 10, the instrument 2 is intended to be engaged in the instrument 1 until the knurl 33 bears against the proximal end of the piece 10 and the ring 12.

Regarding the osteosynthesis material, each screw 3 comprises a screw body 40 intended to be implanted in the pedicle of a vertebra, a threaded proximal slug 41 and a proximal shaft 42 secured to said slug 41 and coaxial thereto. The screw body 40 forms a proximal head 45 for receiving a connecting piece 4 or 5. The screw 3 is in particular of the "polyaxial" type, i.e. with the proximal slug 41 articulated relative to the screw body 40. The proximal shaft 42 comprises, over the entire length thereof, the aforementioned helical track 43.

Each connecting piece 4, 5 comprises a conduit 47 allowing the adjusted engagement of the shaft 6 and a conduit 48 allowing the placement of said connecting piece 4, 5 on the head 45 of the screw body 40.

In reference to FIGS. 14 to 16, it appears that the conduit 48 has a widened proximal part, a narrow middle part and a widened distal part. The wide proximal part is sized so as to allow the engagement therein of the distal end of the instrument 2, and in particular the insertion of the protrusions 19, and comprises two cavities 49 arranged in the wall that defines it, able to receive said protrusions 19 in an adjusted manner. The narrow middle part is sized so as to receive, in an adjusted manner, the distal part 24 of the piece 11 when the protrusions 19 are engaged in the cavities 49 and said piece 11 is brought into the forward position, as visible in FIG. 16. It is visible that this distal part 24 has a slightly conical shape, with a section that increases in the proximal direction, making it possible to engage the distal part 24 in the conduit 48 with progressive wedging. In the wedging position, the handling instrument 1 makes it possible to grasp the connecting piece 4, 5 without play in said connecting piece 4, 5 relative to said instrument 2, both axially and in rotation. The widened distal part of the conduit 48 also allows the engagement of the connecting piece 4, 5 on the head 45 of the screw body 40.

Figure 5:
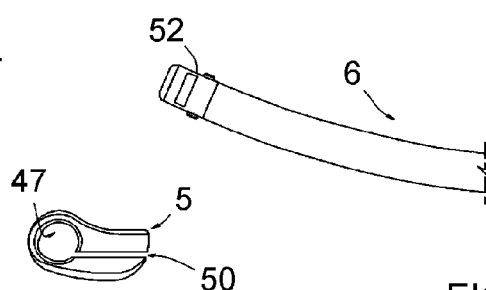

One or more connecting pieces 4 comprised by the osteosynthesis material can be a single piece, as shown in FIGS. 4 and 11 to 16, or one or more connecting pieces 5 comprised by this material can have a middle slot 50 passing through its part defining the conduit 48 until it emerges in the conduit 47, as visible in FIG. 5. Such a piece 5 makes it possible to producing tightening of the connecting bar 6 in the conduit 47 when, once the piece 5 is in place on the head 45 of the screw body 40, an immobilizing nut is screwed on the slug 41.

Figure 6:
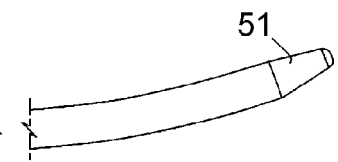

The shaft 6 comprises a slender forward end 51, favoring the dissection of the tissues during insertion thereof, and a rear end 52 allowing it to be grasped in order to be handled. It can be pre-curved, as shown in FIG. 6, or uncurved, as shown in FIGS. 18 to 20.

In practice, the assembly according to the invention makes it possible to implement a percutaneous vertebral osteosynthesis method, four steps of which are shown in FIGS. 17 to 20.

Figure 17:
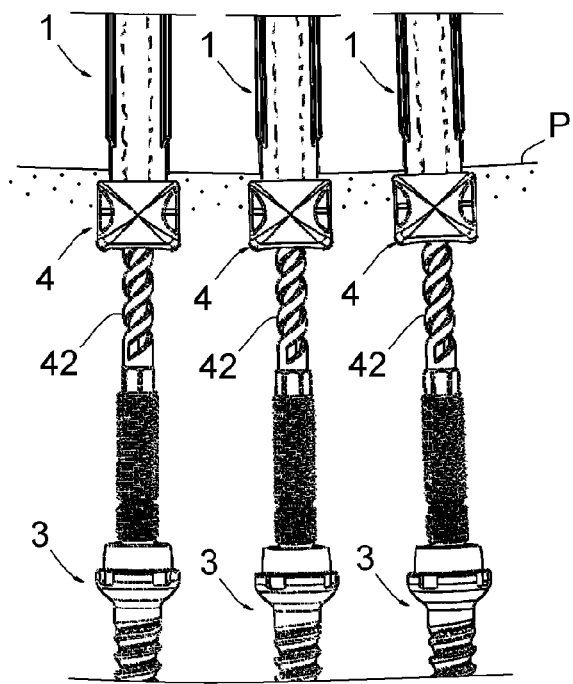
FIGS. 17 to 20 are side views of four successive steps of the implantation of the vertebral osteosynthesis material on the vertebrae of a patient.
Figure 18:
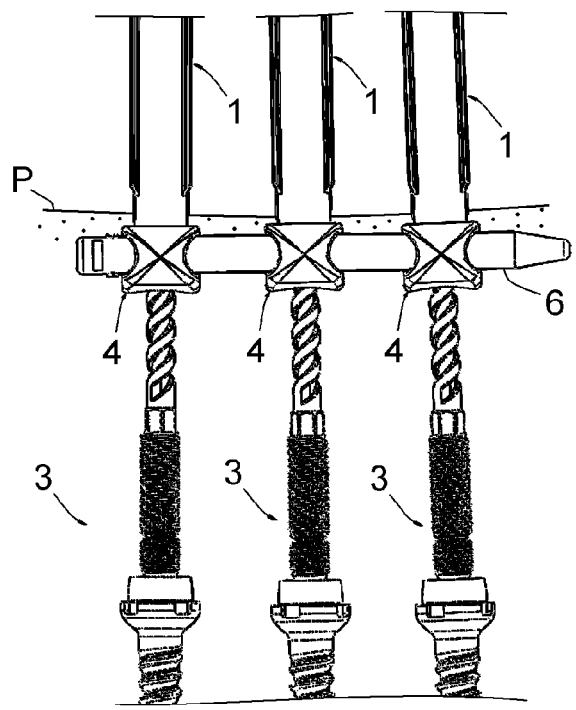
Figure 19:
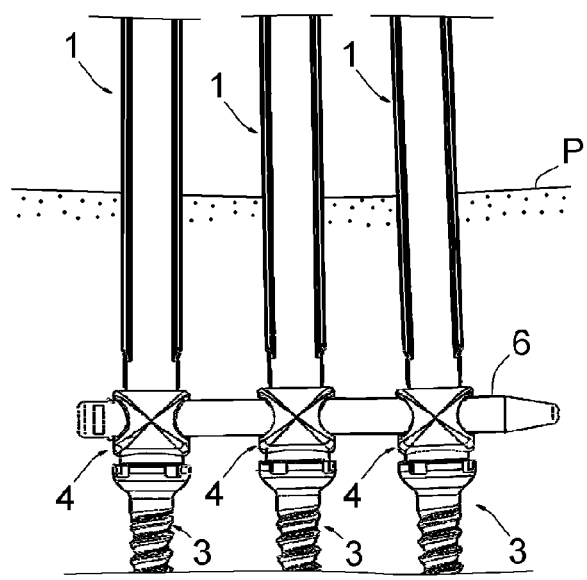
Figure 20:
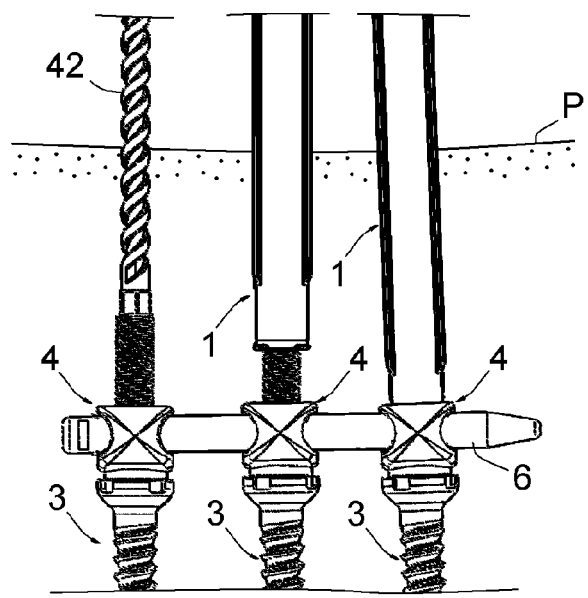

This method consists of:
making only small incisions opposite each implantation area of a screw 3 on a vertebra;
placing the screws 3 on the vertebrae to be treated (not shown in FIGS. 17 to 20); in this implantation position of the screws 3, the proximal shafts 42 protrude past the patient's skin P, as shown in broken lines in FIG. 17;
the connecting pieces 4 or 5 to be implanted being grasped in the aforementioned manner by handling instruments 1, engaging each piece 4, 5 and the instrument 1 on the proximal shaft 42 of a screw 3 and through an incision, until said piece is positioned just under the patient's skin P, cf. FIG. 17;
introducing the connecting bar 6 into said engaging conduit 47 comprised by each connecting piece 4, 5, cf. FIG. 18;
engaging the parts 30 of the engaging instruments 2 in the handling instruments 1 so as to arrange the lugs 35 engaged in the helical tracks 43 of the proximal shafts 42 and to act either on the rotating knurls 33, or on the handle 31 thrusting so as to move the assembly formed by the connecting bar 6 and the connecting pieces 4 or 5 toward the heads 45 of the screw bodies 40, until the connecting pieces 4, 5 are engaged on said heads 45, as shown in FIG. 19;

removing the engaging instruments 2, then separating the handling instruments 1 from the connecting pieces 4, 5 and removing said instruments 1, cf. FIG. 20;

immobilizing the connecting pieces 4, 5 relative to the screws 3 using nuts (not shown);

selecting the slugs 41 at the areas with a smaller section than they comprise; and closing the incisions.

It is understood that the engagement of the connecting bar 6 in the conduits 47 of the connecting pieces 4, 5 is done easily because these connecting pieces are located immediately under the patient's skin P. The connecting bar 6 in fact has a small incline relative to the connecting pieces 4, 5 upon said insertion, and the connecting pieces 4, 5 can be handled and positioned precisely using instruments 1. This ease of insertion of the connecting bar 6 greatly reduces lesions or traumas caused to the tissues surrounding the vertebrae, both between the screws 3 and at the insertion area of the connecting bar 6, and also reduces the operating time.

The dissection of the tissues is done either before inserting the connecting pieces 4, 5 and the connecting bar 6, or by moving said connecting bar 6 and said connecting pieces 4, 5 toward the heads 45 of the screw bodies 40, therefore in the longitudinal direction of the muscular fibers. Such a dissection leads to reduced traumas on the tissues surrounding the vertebrae.

Furthermore, the use of connecting pieces 4, 5 of the "side loading" type makes it possible to avoid instruments 1 whereof the transverse section does not exceed 8 mm in diameter, and is therefore only mildly traumatic for the tissue.

The instruments 2 allow perfect guiding of the connecting pieces 4, 5 toward the heads 45 of the screw bodies 40, and form, with the helical tracks 43, controlled advancement means for the connecting pieces 4, 5. This controlled advancement makes it possible to perform a gradual and controlled dissection of the tissues situated between the incisions.

FIG. 21 shows a screw 3 that is very similar to the one previously described, except that it comprises, instead and in place of the helical track 43, a series of stepped grooves 53.

In reference to FIG. 22, it appears that the instrument 1 usable with this screw 3 comprises pieces 10 and 11 that are similar to those previously described but, in that case, pivotably connected to each other at the distal level. To that end, the piece 11 has eyelets 54 through which pilot points 55 secured to the piece 10 can be engaged. As shown in FIGS. 23 and 24, the piece 10 can pivot relative to the piece 11 between a position separated from said piece 11 (FIG. 23), in which the protrusions 19 and the cavities 49 can engage and disengage, and a position close to each other (FIG. 24), in which these protrusions 19 and cavities 49 are kept engaged.

On the proximal side, the instrument 1 comprises a knurled ring 12 inwardly smooth and laterally open, able to be engaged, with slight elastic deformation, and is pivoted, on smooth proximal portions 56 and 57 respectively formed by the pieces 10 and 11, these proximal portions 67 and 57 jointly forming a proximal cylindrical part of the instrument 1 when the pieces 10 and 11 are in the close position. The distance separating the two ends of the ring 12 that define said lateral opening is slightly smaller than the diameter of the portion 56, making it possible to retain the ring 12 on said portion 56, and that same distance is slightly larger than the width of the portion 57. It is understood that this ring 12 makes it possible, when its lateral opening is not opposite the portion 57, to keep the pieces 10 and 11 in the close position and, when its lateral opening is opposite the portion 57, to free the pivoting of the piece 10 relative to the piece 11.

The piece 11 also comprises, on the distal side, a widened portion 60 in which two diametrically opposite housings 61 are outwardly arranged, the bottoms of said housings 61 being, at their distal ends, pierced with windows emerging in the inner face of the piece 11. These housings 61 are intended to receiving locking hooks 62, the curved ends of which can be engaged through said windows and engage with any of the grooves 53 of the screw 3. The retention of these hooks 62 in said housings 61 is ensured using a laterally open ring 63, which can be engaged, with elastic deformation, on the proximal part of the widened portion 60. This ring 63 is stiff enough to normally keep the hooks 62 in a radially inner position, in which they can engage with one or the other of the grooves 53, but a slight flexibility not preventing the hooks 62 from coming into a radially outer position, in which they are disengaged from said groove 53.

The handling instrument 1 also comprises a proximal eyelet 65 for sliding engagement and guiding of the engagement instrument 2.

The latter part comprises a tubular shaft 30 and a proximal handle 31 to be connected to each other by a shaft 31a, using a transverse pin 36. The shaft 30 has an inner diameter so that it can be engaged on the proximal shaft 42 of the screw 3, and has a conical distal end that can bear against the curved parts of the hooks 62 and thereby bring the latter into said radially outer position.

Figure 25:
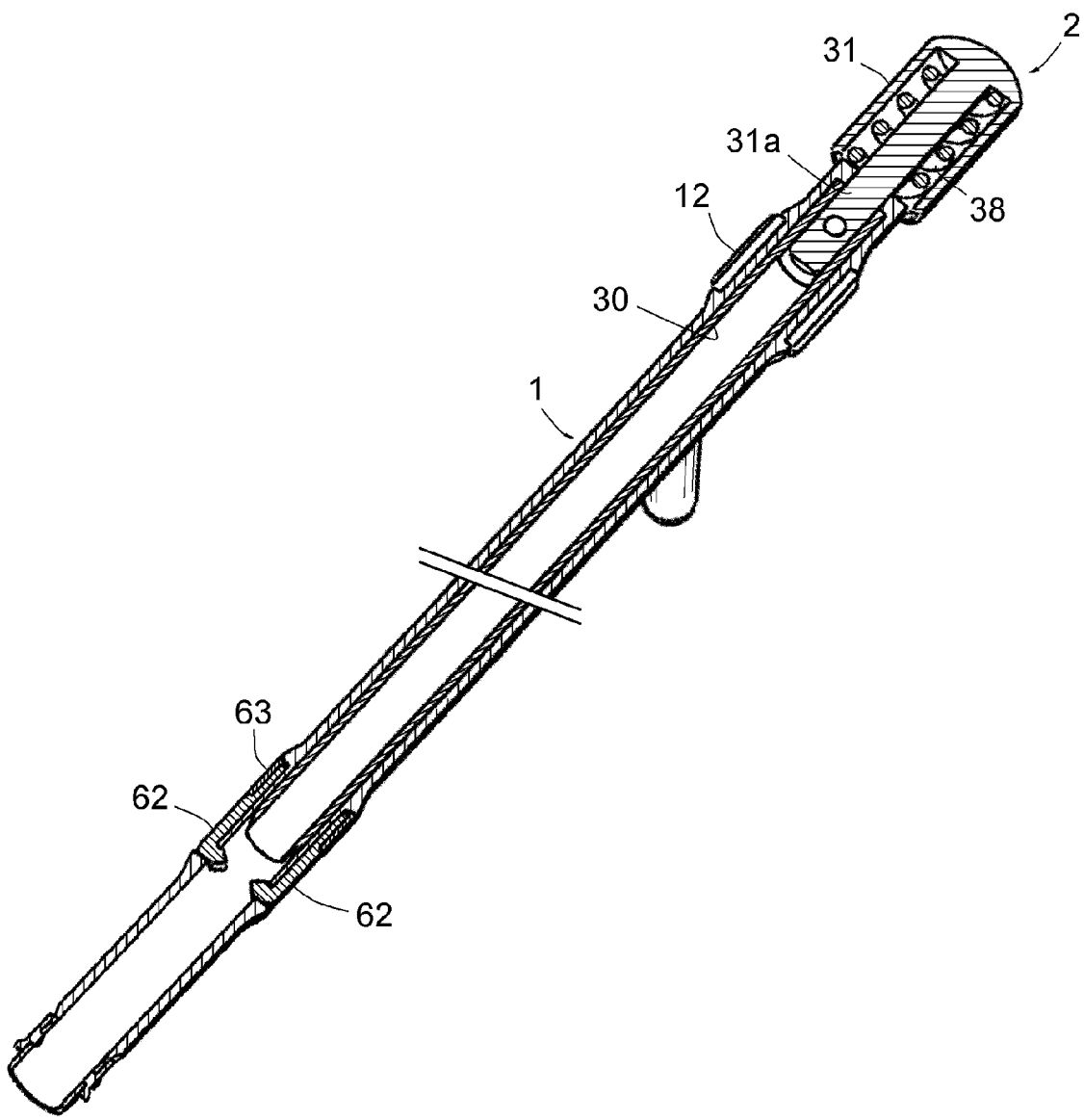
FIG. 25 is a longitudinal cross-sectional view, in the assembled state, of the handling instrument and the engaging instrument according to this second embodiment, the engaging instrument being engaged in the handling instrument.

The instrument 2 also comprises a spring 38 that can be engaged in the handle 31, around the shaft 31a. As shown in FIG. 25, said spring 38 bears, when the engaging instrument 2 is engaged in the handling instrument 1, against the eyelet 65.

In reference to said FIG. 25, it appears that pressure on the handle 31 against the elastic force of the spring 38 makes it possible to slide the shaft 30 into the instrument 1 until actuation, via the conical distal end thereof, of the curved parts of the hooks 62 toward the radially outer position of said hook 62. The grooves 53 and the hooks 62 thus constitute, with the instruments 1 and 2, controlled advancement means for a connecting piece 4 or 5 along a proximal shaft 42 and immobilizing a connecting piece 4 or 5 in a given position along said shaft 42, thereby enabling a gradual placement of the connecting bar 6 and connecting pieces 4, 5, and thereby making it possible to correct the position of the vertebrae.

FIGS. 26 to 31 show a third embodiment of said assembly, simpler than those described above.

In that case, the handling instrument 1 comprises a tube 70 and a gripping handle 71, extending at a right angle relative to the tube 70.

The tube 70 has an oval internal cavity 72 whereof the shape in transverse section is adjusted to the shape of the perimeter of the connecting piece 4 or 5, so that the latter can be inserted narrowly into the distal end of the tube 70, i.e. with sufficient friction to ensure immobilization of the piece 4, 5, in said distal end and retention of said piece 4, 5 in said end. This retention is, however, such that the separation of said piece 4, 5 and of this tube 70 is possible by simply exerting a manual action on the instrument 1.

The tube 70 has a slot 75 emerging in its distal end. This slot 75 has a primary portion whereof the width is slightly larger than that of the slender forward end 51 of one end of the connecting bar 6, and a widened end portion 75a, making it possible to pass the connecting bar 6 through it.

As understood in reference to FIGS. 27 to 31, a screw 3 is placed on a vertebra and a connecting piece 4, 5 intended to be mounted on said screw 3 is inserted and wedged in the distal end of the tube 70. Each piece 10 is lowered on the proximal shaft 42 of the screw 3 and the connecting bar 6 is engaged under the skin in the aforementioned manner.

Figure 29:
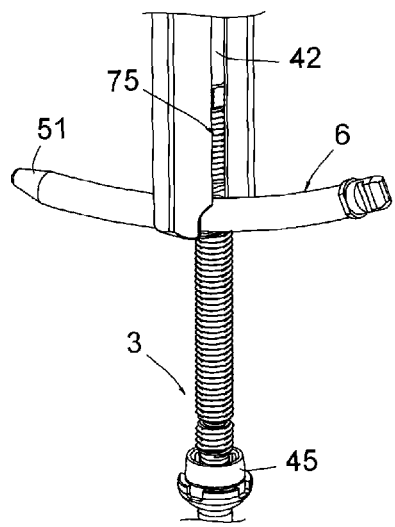
Figure 30:
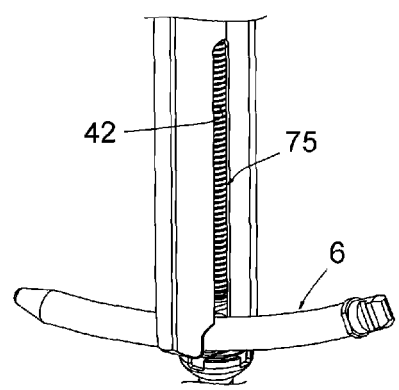
Figure 31:
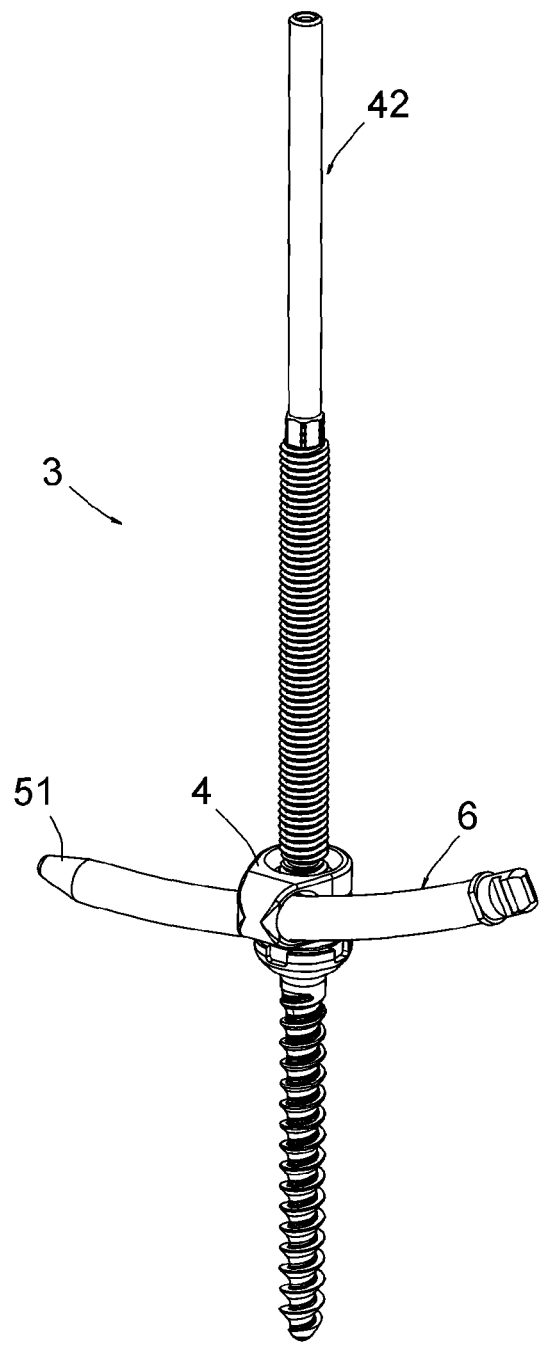

The connecting bar 6 is slid until it abuts against the tube 70 (cf. FIG. 26); the instrument 1 is then slightly raised so as to insert the slender forward end 51 in the slot 75, then is raised so as to slide along said end 51 (cf. FIG. 27) until the end 51 arrives at said widened end portion 75*a* of the slot 75 (cf. FIG. 28) and can thus be guided precisely through the hole of the connecting piece 4, 5 (cf. FIG. 29). The instrument 1 is then lowered again so as to bring the connecting piece 4, 5 into contact with its receiving surface 45 on the screw 3 (cf. FIG. 30), then the instrument 1 is removed (cf. FIG. 31).

Figure 26:
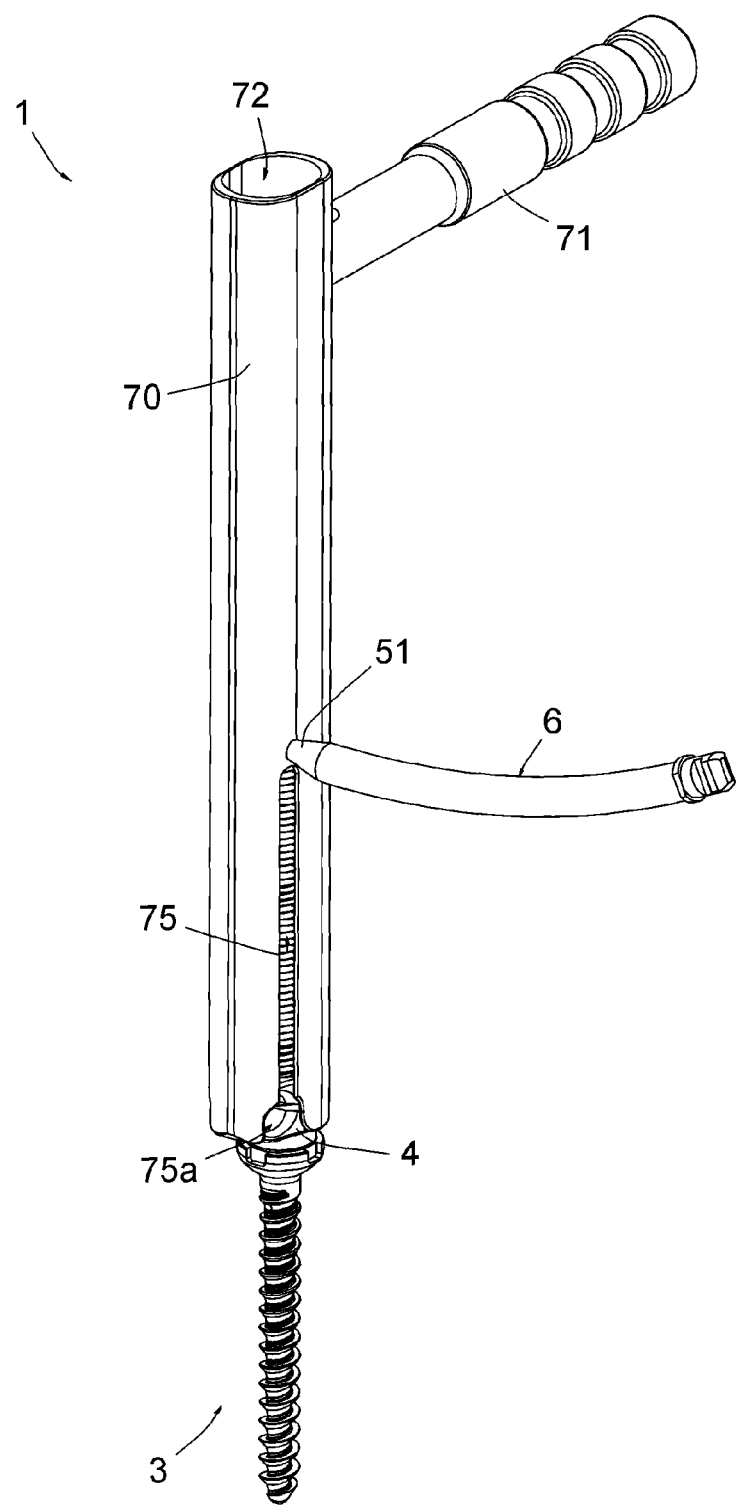
FIG. 26 is a perspective view of a handling instrument according to a third embodiment, engaged on a screw also according to a third embodiment, better visible in FIG. 31; this instrument comprises a connecting piece wedged in its distal end; a connecting bar to be connected to said connecting piece is also shown.
Figure 27:
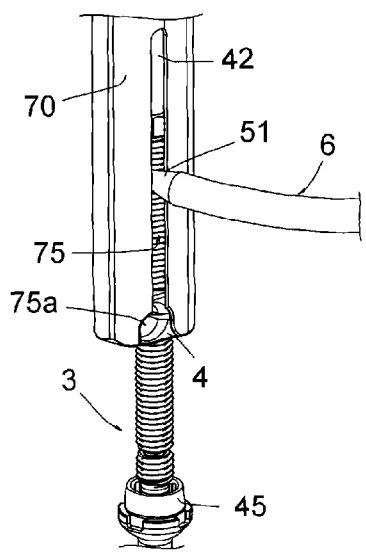
FIGS. 27 to 31 are partial perspective views of the elements of FIG. 26 during five successive steps of the assembly of the connecting bar on the screw.
Figure 28:
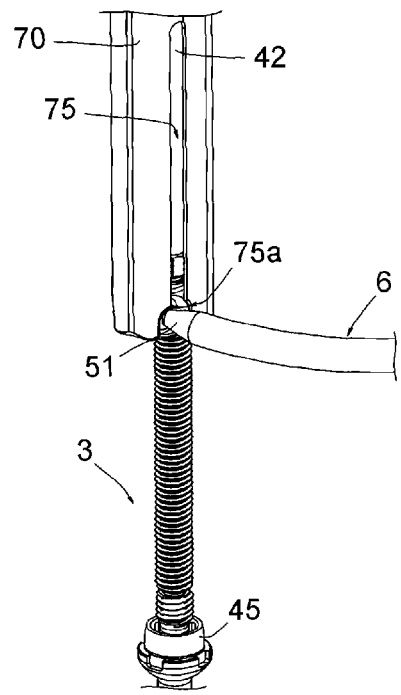

FIGS. 32 and 33 show another connecting piece 4 intended to be used with the instrument 1 shown in FIG. 26. This piece 4 comprises a first portion 4*a* defining the conduit 47 for engaging the bar 6 and a second portion 4*b* defining the conduit 48 for engaging the piece 4 on an anchor screw.

The upper part 4*a*1 of said first portion 4*a* is laterally defined by two straight ends 80 converging toward each other and moving away from said second portion 4*b*, and the lower part 4*a*2 of said first portion 4*a* has two bosses 81 protruding laterally from said lower part 4*a*2, i.e. in a direction parallel to the axis of the conduit 47.

Thus, said first portion 4*a* comprises an upper part 4*a*1 whereof the width is smaller than that of said second portion 4*b*, and a lower part 4*a*2 whereof the width is larger than that of said second portion 4*b*. As shown in FIG. 34, the width of the upper part 4*a*1 is such that, when the connecting piece 4 is grasped using the instrument 1, the edges 80 are significantly pulled back from the wall forming the tube 70 of said instrument, so that said upper part 4*a*1 is not an obstacle to be overcome by said slender forward end 51 of the connecting bar 6. However, the width of said lower part 4*a*2 is such that the boss 81 located at the base of the slot 75 forms a stop for receiving said slender forward end 51. As a result, the latter can be slid into the slot 75 without encountering the part 4*a*, therefore without risking any loss of the guiding allowed by said slot 75; this sliding can be done until the end 51 abuts against the boss 81 (cf. FIG. 35). In that position, said end 51 is perfectly positioned opposite the conduit 47.

As appears from the preceding, the invention provides a vertebral osteosynthesis assembly formed by a vertebral osteosynthesis material and instruments 1 and 2 for placing said material, having the determining advantage of allowing the implantation of the material using a "percutaneous" technique, with an easy connection of a connecting bar 6 with the corresponding screws 3, and by generating lesions or traumas that are as reduced as possible to the tissues surrounding the vertebrae.

The invention has been described above in reference to embodiments provided as examples. It is of course not limited to these embodiments and extends to all other embodiments covered by the appended claims. In particular, the proximal shaft 42 can be threaded, in particular having a threading extending that of the slug 41; the handling instrument 1 and each connecting piece 4, 5 can be shaped so that a connecting piece can be grasped on the outside of said piece, the instrument 1 in this case comprising a distal end able to surround the piece 4, 5, and the latter comprising engaging means at the outer wall thereof.

The invention claimed is:

1. An assembly formed by a vertebral osteosynthesis material and an instrument for placing the material,
the material comprising:
    anchoring members for anchoring to vertebrae of a patient, each of the anchoring members being equipped with a proximal shaft having a length such that the shaft protrudes past the patient's skin when anchored to the vertebrae;
    at least one connecting bar configured to connect several consecutive said anchoring members, the connecting bar having an end; and
    connecting pieces configured to connect the connecting bar to said anchoring members, each of the connecting pieces (i) being distinct and separate from the anchoring members so as to be capable of engaging and sliding axially on the proximal shaft of a said anchoring member when this said anchoring member is anchored to the vertebrae, (ii) comprising a conduit for engaging the connecting bar and a conduit for engaging the proximal shaft of a said anchoring member, and (iii) comprising a first engagement structure situated outside the conduit for engaging the connecting bar and outside the conduit for engaging a said anchoring member; and
the instrument being tubular and comprising:
    at least one distal slot that (i) emerges in a distal end of the instrument, (ii) has a proximal portion, and (iii) has a widened end portion that is wider than the proximal portion;
    a second engagement structure complementary to the first engagement structure and configured to grasp a said connecting piece, this grasping immobilizing the said connecting piece relative to the instrument and not presenting an obstacle, once done, to (i) engagement of the connecting bar in the conduit for engaging the connecting bar of the said connecting piece or (ii) engagement of the said connecting piece on a said anchoring member, wherein:
    each of the connecting pieces comprises a first portion defining the conduit for engaging the connecting bar and a second portion defining the conduit for engaging the proximal shaft of a said anchoring member, the first portion comprising (i) an upper part having a width smaller than a width of the second portion and (ii) a lower part having a width larger than the width of the second portion and that forms a stop below the conduit for engaging the connecting bar, and
    when the instrument grasps a said connecting piece, (i) the conduit for engaging the connecting bar is located in coincidence with the widened end portion of the at least one distal slot of the instrument so that, when the connecting bar rests on the distalmost end of the conduit, the connecting bar is within the widened end portion in a direction perpendicular to the longitudinal direction of the at least one slot, and (ii) the stop is located below the widened end portion, wherein the conduit for engaging the connecting bar is a substantially enclosed circle in cross section and corresponds in diameter to the connecting bar.

2. The assembly according to claim 1, wherein the instrument comprises a single said distal slot, or two said distal slots situated on opposite sides of the instrument.

3. The assembly according to claim 1, wherein:
    the upper part of the first portion is laterally defined by two straight edges converging toward each other and moving away from the second portion, and
    the stop of the lower part of the first portion is at least one boss laterally protruding from the lower part in a direction parallel to the axis of the conduit for engaging the connecting bar.

4. The assembly according to claim 1, wherein the end of the connecting bar is a slender forward end that is configured to be slidingly received and guided in the at least one distal slot of the instrument.

5. The assembly according to claim 1, wherein, for each of the connecting pieces, the conduit for engaging the connecting bar is laterally offset from the axis of the conduit for engaging the proximal shaft of a said anchoring member.

6. The assembly according to claim 1, wherein:
the width of the upper part of the first portion is the dimension of the first portion at the upper part along the axis of the conduit for engaging the connecting bar,
the width of the second portion is the dimension of the second portion along the axis of the conduit for engaging the connecting bar, and
the width of the lower part of the first portion is the dimension of the first portion at the lower part along the axis of the conduit for engaging the connecting bar.

7. The assembly according to claim 1, wherein in a plan view taken along the axis of the conduit for engaging the proximal shaft of a said anchoring member, the stop of each of the connecting members projects outward from the upper part of the first portion.

8. Percutaneous vertebral osteosynthesis method using the assembly according to claim 1, including the following steps:

making only small incisions opposite each implantation area of a said anchoring member on a vertebra of a patient;

placing the anchoring members on the vertebrae to be treated;

using the instrument to grasp at least one of the connecting pieces, place the at least one connecting piece on the proximal shaft of a said anchoring member, and position the at least one connecting piece just under the patient's skin through a said incision;

introducing the connecting bar just under the patient's skin and then engaging the connecting bar in the conduit for the connecting bar of a said connecting piece;

repeating, if necessary, the using and introducing operations to engage a required number of said connecting pieces on the connecting bar;

moving the assembly formed by the connecting bar and the connecting pieces toward receiving surfaces for the connecting pieces of the anchoring members;

immobilizing the connecting pieces relative to the anchoring members using immobilization members comprised by the material; and closing the incisions.

\* \* \* \* \*